United States Patent
Barth et al.

(10) Patent No.: US 7,320,978 B2
(45) Date of Patent: Jan. 22, 2008

(54) OXAZOLE DERIVATIVES, PREPARATION AND THERAPEUTIC USE THEREOF

(75) Inventors: Francis Barth, Saint Georges d'Orques (FR); Joelle Arnaud-Taillades, Montpellier (FR); Christian Congy, Saint Gely du Fesc (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 4 days.

(21) Appl. No.: 11/461,629

(22) Filed: Aug. 1, 2006

(65) Prior Publication Data

US 2007/0043060 A1    Feb. 22, 2007

Related U.S. Application Data

(63) Continuation of application No. PCT/FR2005/000321, filed on Feb. 11, 2005.

(30) Foreign Application Priority Data

Feb. 13, 2004    (FR) .................................. 04 01507

(51) Int. Cl.
*A61K 31/422*    (2006.01)
*A61K 31/445*    (2006.01)
*A61K 31/496*    (2006.01)
*C07D 413/02*    (2006.01)
*C07D 263/30*    (2006.01)

(52) U.S. Cl. ................. 514/252.13; 544/224; 544/358; 544/366; 544/369; 546/184; 546/192; 546/207; 546/209; 548/215; 548/235; 548/236; 514/252.12; 514/315; 514/326; 514/374

(58) Field of Classification Search ................ 344/224, 344/336, 358, 359, 366, 367, 369; 546/184, 546/192, 207, 209; 548/215, 236; 514/252.12, 514/326, 374

See application file for complete search history.

(56) References Cited

U.S. PATENT DOCUMENTS 3,622,595 A * 11/1971 Marchetti .................. 548/236

3,925,404 A * 12/1975 Marchetti .................. 548/236

FOREIGN PATENT DOCUMENTS

| FR | 2085675 | 12/1971 |
|---|---|---|
| WO | WO 94/27980 | 12/1994 |
| WO | WO 96/36617 | 11/1996 |
| WO | WO 00/46209 | 8/2000 |
| WO | WO 03/007887 | 1/2003 |
| WO | WO 03/027076 | 4/2003 |
| WO | WO 03/063781 | 8/2003 |
| WO | WO 03/078413 | 9/2003 |
| WO | WO 03/082191 | 10/2003 |
| WO | WO 2004/065374 | 8/2004 |

OTHER PUBLICATIONS

Rinaldi-Carmona, M., et. al., SR141716A, A Potent and Selective Antogonist of the Brain Cannabinoid Receptor, Febs Letters, Elsevier Science Publishers, Amsterdam, NL, vol. 350, No. 2/3, (1994) pp. 240-244.

* cited by examiner

*Primary Examiner*—Golam M. M. Shameem
(74) *Attorney, Agent, or Firm*—Balaram Gupta

(57) ABSTRACT

This invention relates to compounds of formula (I):

Wherein $R_1$, $R_2$, $R_3$, $R_4$, $R_5$, $R_6$, $R_7$ and $R_8$ are as described herein. The invention further relates to a method for prevention and therapeutic use thereof.

11 Claims, No Drawings

OXAZOLE DERIVATIVES, PREPARATION AND THERAPEUTIC USE THEREOF

CROSS REFERENCE TO RELATED APPLICATIONS

This application is a continuation of International application No. PCT/FR2005/000,321, filed Feb. 11, 2005, which is incorporated herein by reference in its entirety; which claims the benefit of priority of French Patent Application No. 04/01,507, filed Feb. 13, 2004.

BACKGROUND OF THE INVENTION

1. Field of the Invention

The present invention relates to 4,5-diaryl-1,3-oxazole-2-carboxamide derivatives, to the preparation thereof and to the use thereof in therapeutics.

2. Description of the Art

French Patent Application FR 2 085 675 describes compositions of formula:

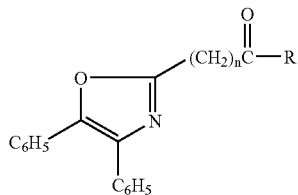

The therapeutic indications described for these compounds are: inflammations of the respiratory system, locomotor system traumas, and edemas of all types.

SUMMARY OF THE INVENTION

A subject of the present invention is compounds corresponding to the formula:

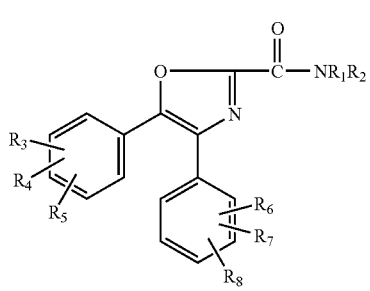

in which:

$R_1$ represents hydrogen or a $(C_1-C_4)$alkyl;

$R_2$ represents:
- a $(C_4-C_{10})$alkyl group;
- a nonaromatic $C_3-C_{12}$ carbocyclic radical that is unsubstituted or substituted one or more times with a $(C_1-C_4)$alkyl group;
- a 1,2,3,4-tetrahydronaphth-1-yl or -2-yl;
- a saturated, monooxygenated or monosulfur-containing heterocyclic radical having from 5 to 7 atoms, that is unsubstituted or substituted one or more times with a $(C_1-C_4)$alkyl group;
- a saturated, mononitrogenous heterocyclic radical having from 5 to 7 atoms, the nitrogen atom being substituted with a $(C_1-C_4)$alkyl, phenyl, benzyl, $(C_1-C_4)$alkoxycarbonyl or $(C_1-C_4)$alkanoyl group;
- a $(C_1-C_3)$alkylene group carrying a nonaromatic $C_3-C_{12}$ carbocyclic radical that is unsubstituted or substituted one or more times with a $(C_1-C_4)$ alkyl group;
- a phenylalkylene group in which the alkylene is $(C_1-C_3)$, that is unsubstituted or substituted on the alkylene with one or more methyl or $(C_1-C_4)$alkoxycarbonyl groups, and unsubstituted or substituted on the phenyl with one or more substituents, that may be identical or different, chosen from a halogen atom or a $(C_1-C_4)$alkyl, trifluoromethyl, $(C_1-C_4)$alkoxy, or trifluoromethoxy group;
- a group $NR_9R_{10}$;

or $R_1$ and $R_2$, together with the nitrogen atom to which they are attached, constitute
  - either a piperazin-1-yl or 1,4-diazepan-1-yl radical substituted in the 4-position with a phenyl or benzyl group;
  - or a piperidin-1-yl or pyrrolidin-1-yl radical mono- or disubstituted with groups, that may be identical or different, chosen from a phenyl, benzyl, $(C_1-C_4)$ alkyl, hydroxyl, cyano, $(C_1-C_3)$alkanoyl, $(C_1-C_4)$ alkoxycarbonyl or $(C_1-C_4)$alkoxycarbonylamino group, or with a group $CONR_{11}R_{12}$ or $NR_{11}R_{12}$;
    the phenyl or benzyl groups substituting said radicals being unsubstituted or substituted with one or more substituents chosen from a halogen atom, or a methyl, hydroxyl, methoxy, cyano, acetyl or methoxycarbonyl group;
  - or a spiro[1H-inden-1,4'-piperidine] radical or a 3H-spiro[2-benzofuran-1,4'-piperidine] radical, said radical being unsubstituted or substituted with an oxo group;

$R_3$, $R_4$, $R_5$, $R_6$, $R_7$ and $R_8$ each represent, independently of one another, a hydrogen or halogen atom, a $(C_1-C_6)$ alkyl, $(C_1-C_6)$alkoxy or trifluoromethyl group or a group $S(O)_n$Alk; on the condition that $R_3$, $R_4$, $R_5$, $R_6$, $R_7$ and $R_8$ are not simultaneously a hydrogen atom;

$R_9$ represents a hydrogen atom or a methyl group;

$R_{10}$ represents a $(C_3-C_6)$alkyl, phenyl or $(C_3-C_{10})$cycloalkyl group, said phenyl and cycloalkyl groups being unsubstituted or substituted with one or more substituents chosen from a halogen atom or a $(C_1-C_4)$ alkyl group;

or $R_9$ and $R_{10}$, together with the nitrogen atom to which they are attached, constitute a saturated or unsaturated heterocyclic radical having from 5 to 11 atoms, which may or may not be bridged, possibly comprising a spiro carbon and possibly containing a second hetero atom chosen from O or N, said radical being unsubstituted or substituted one or more times with a substituent group chosen from a hydroxyl, $(C_1-C_4)$alkyl or $(C_1-C_4)$ alkoxycarbonyl group or a phenyl group that is unsubstituted or substituted with one or more substituents chosen from a halogen atom or a $(C_1-C_4)$alkyl group;

$R_{11}$ and $R_{12}$ each represent, independently of one another, a hydrogen atom or a $(C_1-C_4)$alkyl group, or $R_{11}$ and $R_{12}$, together with the nitrogen atom to which they are attached, constitute a saturated heterocyclic radical having from 3 to 7 atoms, possibly containing a second hetero atom chosen from O or N, said heterocyclic radical being unsubstituted or substituted one or more times with a methyl;

n represents 0, 1 or 2;

Alk represents a $(C_1-C_4)$alkyl group;

and also their salts, their solvates and their hydrates.

DETAILED DESCRIPTION OF THE INVENTION

The compounds of formula (I) may contain one or more asymmetric carbon atoms. They may therefore exist in the form of enantiomers or of diastereoisomers. These enantiomers and diastereoisomers, and also mixtures thereof, including racemic mixtures, form part of the invention.

The compounds of formula (I) may exist in the form of bases or of addition salts with acids. These salts are advantageously prepared with pharmaceutically acceptable salts, but the salts of other acids that are useful, for example, for purifying or isolating the compounds of formula (I) also form part of the invention.

The compounds of formula (I) may also exist in the form of hydrates or of solvates, i.e. in the form of associations or of combinations with one or more molecules of water or with a solvent. Such hydrates and solvates also form part of the invention.

The term "alkyl" group is intended to mean a linear or branched radical such as, in particular: methyl, ethyl, propyl, isopropyl, butyl, isobutyl, tert-butyl, n-pentyl, isopentyl, n-hexyl or isohexyl, the methyl group being preferred for a $(C_1-C_4)$alkyl, the tert-butyl, 2-methyl-2-butyl and 3,3-dimethyl-2-butyl groups being preferred for a $(C_3-C_6)$alkyl.

The term "alkylene group" is intended to mean a linear or branched divalent radical, methylene, 1-methylmethylene and ethylene being preferred.

The term "alkoxy group" is intended to mean a linear or branched radical, the methoxy group being preferred.

The term "halogen atom" is intended to mean a fluorine, chlorine, bromine or iodine atom, fluorine, chlorine or bromine atoms being preferred.

The nonaromatic $C_3-C_{12}$ carbocyclic radicals comprise monocyclic or polycyclic, fused or bridged radicals. The monocyclic radicals include cycloalkyls, for example cyclopropyl, cyclobutyl, cyclopentyl, cyclohexyl, cycloheptyl or cyclooctyl, cyclohexyl and cyclopentyl being preferred. The fused, bridged or spiro-form di- or tricyclic radicals include, for example, norbornyl, bornyl, isobornyl, noradamantyl, adamantyl, spiro[5.5]undecyl, bicyclo[2.2.1]heptyl, bicyclo[3.2.1]octyl and bicyclo[3.1.1]heptyl radicals.

The expression "saturated or unsaturated heterocyclic radical having from 3 to 11 atoms, possibly containing a second hetero atom such as O or N" is intended to mean radicals such as aziridinyl, azetidinyl, morpholin-4-yl, piperidin-1-yl, piperazin-1-yl, pyrrolidin-1-yl or octahydrocyclopenta[c]pyrrol-2-yl, the piperidin-1-yl and morpholin-4-yl radicals being preferred.

The expression "saturated mononitrogenous heterocyclic radical having from 5 to 7 atoms" is intended to mean a radical such as piperidin-4-yl or pyrrolidin-3yl, piperidin-4-yl radical being preferred.

The expression "saturated monooxygenated heterocyclic radical having from 5 to 7 atoms" is intended to mean a radical such as tetrahydrofuranyl, tetrahydro-2H-pyranyl or oxepanyl, tetrahydrofuranyl being preferred.

The expression "saturated, monosulfur-containing heterocycle having from 5 to 7 atoms" is intended to mean a radical such as tetrahydrothienyl, tetrahydro-2H-thiopyranyl or thiepanyl.

According to the present invention, the compounds of formula (I) that are distinguished are those in which:

$R_1$ and $R_2$, together with the nitrogen atom to which they are attached, constitute either a piperazin-1-yl or 1,4-diazepan-1-yl radical substituted in the 4-position with a phenyl or benzyl group;

or a piperidin-1-yl or pyrrolidin-1-yl radical that is monosubstituted or gem-disubstituted with groups, that may be identical or different, chosen from a phenyl, benzyl, $(C_1-C_4)$alkyl, hydroxyl, $(C_1-C_3)$alkanoyl, $(C_1-C_4)$alkoxycarbonyl or $(C_1-C_4)$alkoxycarbonylamino group;

the phenyl or benzyl groups substituting said radicals being unsubstituted or substituted with one or more substituents chosen from a halogen atom and a methyl group;

$R_3$, $R_4$, $R_5$, $R_6$, $R_7$ and $R_8$ each represent, independently of one another, a hydrogen or halogen atom, a $(C_1-C_6)$alkyl, $(C_1-C_6)$alkoxy or trifluoromethyl group or a group $S(O)_n$Alk; on the condition that $R_3$, $R_4$, $R_5$, $R_6$, $R_7$ and $R_8$ are not simultaneously a hydrogen atom;

n represents 0, 1 or 2;

Alk represents a $(C_1-C_4)$alkyl group;

and also their salts, their solvates and their hydrates.

According to the present invention, particularly distinguished are the compounds of formula (I) in which:

$R_1$ and $R_2$, together with the nitrogen atom to which they are attached, constitute:

either a piperazin-1-yl radical substituted in the 4-position with a benzyl or phenyl group;

or a piperidin-1-yl radical that is monosubstituted or disubstituted with a phenyl, benzyl, $(C_1-C_4)$alkyl, hydroxyl, cyano, $(C_1-C_3)$alkanoyl, $(C_1-C_4)$alkoxycarbonyl or $(C_1-C_4)$alkoxycarbonylamino group, or with a group $CONR_{11}R_{12}$ or $NR_{11}R_{12}$;

the phenyl or benzyl groups substituting said radicals being unsubstituted or substituted with one or more substituents chosen from a halogen atom, or a methyl, methoxy, cyano, acetyl or methoxycarbonyl group;

or a spiro[1H-inden-1,4'-piperidine] radical or a 3H-spiro[2-benzofuran-1,4'-piperidine] radical, said radical being unsubstituted or substituted with an oxo group;

$R_{11}$ and $R_{12}$ each represent, independently of one another, a hydrogen atom or a $(C_1-C_4)$alkyl group, or $R_{11}$ and $R_{12}$, together with the nitrogen atom to which they are attached, constitute a saturated heterocyclic radical having from 3 to 7 atoms, possibly containing a second hetero atom chosen from O or N, said heterocyclic radical being unsubstituted or substituted one or more times with a methyl;

$R_3$, $R_4$, $R_5$, $R_6$, $R_7$ and $R_8$ each represent, independently of one another, a hydrogen or halogen atom; on the condition that $R_3$, $R_4$, $R_5$, $R_6$, $R_7$ and $R_8$ are not simultaneously a hydrogen atom; preferably, $R_3$ represents a 4-chloro or 4-bromo, and $R_6$ represents a 2-chloro, $R_7$ represents a 4-chloro or a hydrogen atom, and $R_4$, $R_5$, and $R_8$ represent a hydrogen atom;

and also their salts, their solvates and their hydrates.

According to the present invention, most particularly distinguished are the compounds of formula (I) in which:

$R_1$ and $R_2$, together with the nitrogen atom to which they are attached, constitute:

either a piperazin-1-yl radical substituted in the 4-position with a phenyl group;

or a piperidin-1-yl radical that is unsubstituted or gem-disubstituted with a phenyl or piperidin-1-yl group, and with a cyano, acetyl, aminocarbonyl or pyrrolidin-1-ylcarbonyl group;

the phenyl group substituting said radicals being unsubstituted or substituted with a chlorine, bromine or fluorine atom, or with a methyl, methoxy, hydroxyl, cyano or acetyl group;

or a spiro[1H-inden-1,4'-piperidine] radical or a 3H-spiro[2-benzofuran-1,4'-piperidin]-3-one radical;

$R_3$ is a 4-bromo or a 4-chloro;

$R_6$ is a 2-chloro;

$R_7$ is a 4-chloro or a hydrogen atom;

$R_4$, $R_5$ and $R_8$ represent a hydrogen atom;

and also their salts, their solvates or their hydrates.

The following compounds are preferred:

1-{[5-(4-Chlorophenyl)-4-(2,4-dichlorophenyl)-1,3-oxazol-2-yl]carbonyl}-4-(3-methylphenyl)piperazine.

1-{[5-(4-Chlorophenyl)-4-(2,4-dichlorophenyl)-1,3-oxazol-2-yl]carbonyl}-4-(3-methylphenyl)piperazine.

1-{[5-(4-Chlorophenyl)-4-(2,4-dichlorophenyl)-1,3-oxazol-2-yl]carbonyl}-4-(4-chlorphenyl)piperazine.

1-{[5-(4-Chlorophenyl)-4-(2,4-dichlorophenyl)-1,3-oxazol-2-yl]carbonyl}-4-(3-fluorophenyl)piperazine.

1-{[5-(4-Chlorophenyl)-4-(2,4-dichlorophenyl)-1,3-oxazol-2-yl]carbonyl}-4-(2-chlorophenyl)piperazine.

1-(4-(4-Chlorophenyl)-1-{[5-(4-chlorophenyl)-4-(2,4-dichlorophenyl)-1,3-oxazol-2-yl]carbonyl}piperidin-4-yl)ethanone.

1-{[5-(4-Chlorophenyl)-4-(2,4-dichlorophenyl)-1,3-oxazol-2-yl]carbonyl}-4phenylpiperidine-4-carboxamide.

1-[4-(4-{[5-(4-Chlorophenyl)-4-(2,4-dichlorophenyl)-1,3-oxazol-2-yl]carbonyl}piperazin-1-yl)phenyl]ethanone.

1'-{[5-(4-Chlorophenyl)-4-(2,4-dichlorophenyl)-1,3-oxazol-2-yl]carbonyl}-1,4'-bipiperidine-4'-carboxamide.

1-(1-{[4-(2-Chlorophenyl)-5-(4-chlorophenyl)-1,3-oxazol-2-yl]carbonyl}-4-phenylpiperidin-4-yl)ethanone.

1-{[5-(4-Chlorophenyl)-4-(2,4-dichlorophenyl)-1,3-oxazol-2-yl]carbonyl}-4-phenylpiperidine-4-carbonitrile.

1-(3-Chlorophenyl)-4-{[4-(2-chlorophenyl)-5-(4-chlorophenyl)-1,3-oxazol-2-yl]carbonyl}piperazine.

1'-{[5-(4-Chlorophenyl)-4-(2-chlorophenyl)-1,3-oxazol-2-yl]carbonyl}1-1,4'bipiperidine-4'-carboxamide.

The following compounds are most particularly preferred:

1-(1-{[5-(4-Bromophenyl)-4-(2,4-dichlorophenyl)-1,3-oxazol-2-yl]carbonyl}4-phenylpiperidin-4-yl)ethanone.

1-(1-{[5-(4-Bromophenyl)-4-(2,4-dichlorophenyl)-1,3-oxazol-2-yl]carbonyl}-4-(3-chrolorphenyl)piperazine.

1-(1-{[5-(4-Chlorophenyl)-4-(2,4-dichlorophenyl)-1,3-oxazol-2-yl]carbonyl}-4phenylpiperidin-4-yl)ethanone.

A subject of the present invention is also a process for preparing the compounds according to the invention.

This process is characterized in that the acid of formula (II) or a functional derivative of this acid of formula:

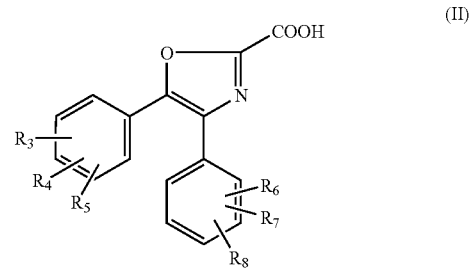

in which $R_3$, $R_4$, $R_5$, $R_6$, $R_7$ and $R_8$ are as defined for (I), is treated with an amine of formula $HNR_1R_2$ (III) in which $R_1$ and $R_2$ are as defined for (I). Optionally, the compound thus obtained is converted to one of its salts or solvates.

As functional derivative of the acid (II), use may be made of the acid chloride, the anhydride, a mixed anhydride, a $C_1$-$C_4$ alkyl ester in which the alkyl is straight or branched, an activated ester, for example the ester of p-nitrophenyl, or the free acid opportunistically activated, for example, with N,N-dicyclohexylcarbodiimide or with benzotriazol-1-yloxotris(dimethylamino)phosphonium hexafluorophosphate (BOP) or benzotriazol-1-yloxotris(pyrrolidino)phosphonium hexafluorophosphate (PyBOP).

Thus, in the process according to the invention, 1,3-oxazole-3-carboxylic acid or its chloride, obtained by reaction of thionyl chloride with the acid of formula (II), can be reacted with an amine $HNR_1R_2$, in an inert solvent, such as a chlorinated solvent (dichloromethane, dichloroethane, chloroform, for example), an ether (tetrahydrofuran, dioxane, for example), or an amide (N,N-dimethylformamide, for example) under an inert atmosphere, at a temperature of between 0° C. and ambient temperature, in the presence of a tertiary amine such as triethylamine, N-methylmorpholine or pyridine (method A).

It is also possible to react an alkyl ester of the compound of formula (II) with an amine $NHR_1R_2$, in an inert solvent, in the presence of trimethylaluminum (method B).

A variant consists in preparing the mixed anhydride of the acid of formula (II) by reaction of ethyl chloroformate with the acid of formula (II), in the presence of a base such as triethylamine, and in reacting thus formed mixed anhydride with an amine $HNR_1R_2$, in a solvent such as dichloromethane, under an inert atmosphere, at ambient temperature, in the presence of a base such as triethylamine.

The compounds of formula (II) can be prepared according to the scheme below:

SCHEME 1

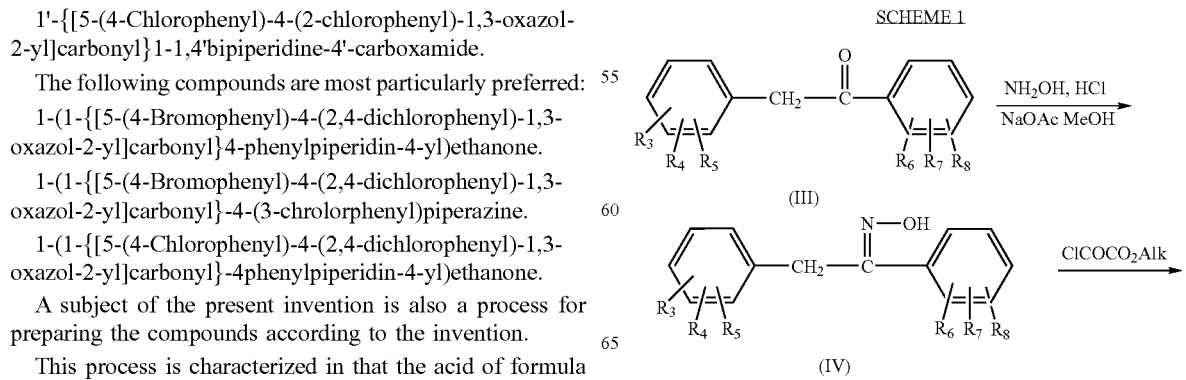

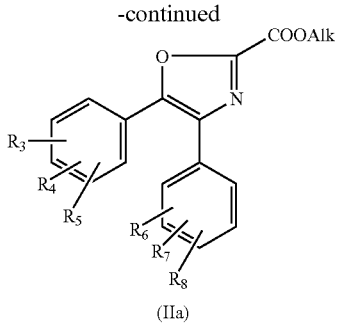

(IIa)

The compound of formula (III) can be prepared by known methods as described in patent application WO 03/07887, by means of the action of a derivative of phenylacetic acid on a benzoic acid ester in the presence of NaHMDS (sodium hexamethyldisilazane).

The oxime of formula (IV) is obtained by means of the action of hydroxylamine hydrochloride on the compound of formula (III).

The cyclization is then carried out by means of the action of an alkyl oxalate halide.

Methyl and ethyl esters of 4,5-diphenyl-1,3-oxazole-2-carboxylic acid are described in U.S. Pat. No. 3,622,595 and in the publication, Yakugaku Zasshi, 1962, 82,140-143.

The acids of formula (II) and the esters of formula (IIa) are novel when $R_3$, $R_4$, $R_5$, $R_6$, $R_7$ and $R_8$ are other than hydrogen.

Thus, a subject of the present invention is also the compounds of formula:

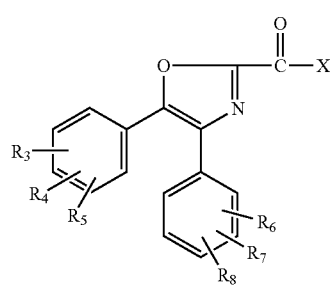

(IIb)

in which:
X represents a halogen atom, or a hydroxyl, $(C_1-C_4)$alkyl or benzyl group;
$R_3$, $R_4$, $R_5$, $R_6$, $R_7$ and $R_8$ each represent, independently of one another, a hydrogen or halogen atom, a $(C_1-C_6)$ alkyl, $(C_1-C_6)$alkoxy or trifluoromethyl group or a group $S(O)_n$Alk;
Alk represents a $(C_1-C_4)$alkyl;
n represents 0, 1 or 2;
on the condition that $R_3$, $R_4$, $R_5$, $R_6$, $R_7$ and $R_8$ are not simultaneously hydrogen.

When X represents an OH group, the compounds of formula (IIb) can also exist in the form of salts. Such salts form part of the invention.

According to the present invention, 5-(4-chlorophenyl)-4-(2,4-dichlorophenyl)-1,3-oxazole-2-carboxylic acid, 5-(4-bromophenyl)-4-(2,4-dichlorophenyl)-1,3-oxazole-2-carboxylic acid, 5-(4-chlorophenyl)-4-(2-chlorophenyl)-1,3-oxazole-2-carboxylic acid and 5-(2,4-dichlorophenyl)-(4-chlorophenyl)-1,3-oxazole-2-carboxylic acid, their ethyl esters and their chlorides are preferred.

The following examples describe the preparation of certain compounds in accordance with the invention. These examples are not limiting and merely illustrate the present invention. The numbers of the compounds exemplified refer to those given in the table hereinafter, which illustrates the chemical structures and the physical properties of some compounds according to the invention.

In the examples, the following abbreviations are used:
Mp: melting point
BOP: benzotriazol-1-yloxytris(dimethylamino)phosphonium hexafluorophosphate.
THF: tetrahydrofuran
AT: ambient temperature
DCM: dichloromethane
MeOH: methanol.

The nuclear magnetic resonance spectra are recorded at 200 MHz in DMSO-$d_6$. For the interpretation of the spectra, the following abbreviations are used: s: singlet, d: doublet, t: triplet, up: unresolved peak, mt: multiplet, bs: broad singlet.

The compounds according to the invention are analyzed by LC/UV/MS coupling (liquid chromatography/UV detection/mass spectrometry) according to the conditions (a) or (b) described hereinafter. The molecular peak (MH$^+$) and the retention time (rt) in minutes are measured.

Conditions (a):
A Waters® XTerra MS C18 column sold by Waters, that is 2.1×50 mm and 3.5 µm is used, at 30° C., with a flow rate of 0.4 ml/minute.
The eluent is composed as follows:
solvent A: 10 mM ammonium acetate (NH$_4$OAc) in water at pH 7;
solvent B: acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV dectection is carried out at λ=220 nm and the mass detection is carried out in the positive ESI chemical ionization mode.

Conditions (b):
A Waters® Xterra MS C18 column, sold by Waters, that is 2.1×30 mm and 3.5 µm is used, at ambient temperature, with a flow rate of 1 ml/minute.
The eluent is composed as follows:
solvent A: 0.025% of trifluoroacetic acid (TFA) in water
solvent B: 0.025% of TFA in acetonitrile.
Gradient: the percentage of solvent B ranges from 0 to 100% in 2 minutes, with a plateau at 100% of B for 1 minute.
The UV detection is carried out between 210 nm and 400 nm and the mass detection is carried out in the chemical ionization mode at atmospheric pressure.

EXAMPLE 1

Compound No. 1

5-(4-Chlorophenyl)-4-(2,4-dichlorophenyl)-N-piperidin-1-yl-1,3-oxazole-2-carboxamide

1.1: 5-(4-Chlorophenyl)-4-(2,4-dichlorophenyl)-1,3-oxazole-2-carboxylic acid ethyl ester

1.1.1: 2-(4-Chlorophenyl)-1-(2,4-dichlorophenyl)ethanone

This compound is prepared according to procedures set out in patent application WO 03/007887, which is hereby incorporated by reference in its entirety.

1.1.2: 2-(4-Chlorophenyl)-1-(2,4-dichlorophenyl)ethanoneoxime 2.15 g of the compound from the preceding step are suspended in 32 ml of MeOH, and a mixture of 3 g of hydroxylamine hydrochloride and 5.40 g of sodium acetate, in solution in 21 ml of water are added, and the reaction mixture is refluxed for 18 hours. It is concentrated under vacuum to half the volume, and then 50 ml of water are added. The reaction medium is extracted with DCM and then washing is carried out with water and then a saturated NaCl solution. 2.24 g of the expected compound are obtained, Mp=91° C.

1.1.3: 5-(4-Chlorophenyl)-4-(2,4-dichlorophenyl)-1,3-oxazole-2-carboxylic acid ethyl ester 1.28 ml of ethyl oxalate chloride are added drop wise onto 1.20 g of the oxime obtained in the preceding step, the reaction mixture is stirred for 15 minutes at AT, and is then heated at 120° C. for 2 hours. The reaction medium is then poured into 50 ml of ice-cold water. The mixture is extracted with DCM, and then washing is carried out with a saturated NaHCO$_3$ solution followed by a saturated NaCl solution. After drying over MgSO$_4$, the product obtained is chromatographed on silica, elution being carried out with an EtOAc/hexane mixture (8/92; v/v). 0.51 g of the expected compound is obtained.

1.2: 5-(4-Chlorophenyl)-4-(2,4-dichlorophenyl)-1,3-oxazole-2-carboxylic acid A solution containing 1.02 g of the ester obtained in the preceding step in 25 ml of MeOH, 5 ml of TBF and 0.2 ml of water is prepared, and 0.123 g of LiOH is added. The reaction medium is stirred at AT for 1 hour 30 minutes, and then poured into a 5% HCl solution cooled to 0° C. The precipitate obtained is filtered off and then washed with water and dried under vacuum. 0.72 g of the expected compound is obtained, Mp=90° C.

1.3: 5-(4-Chlorophenyl)-4-(2,4-dichlorophenyl)-N-piperidin-1-yl-1,3-oxazole-2-carboxamide A solution of the acid obtained in the preceding step in 15 ml of DCM and 1.5 ml of THF is prepared, and 0.68 ml of triethylamine is added, followed by 0.22 ml of 1-aminopiperidine, and then, at 0° C., 0.91 g of BOP. The reaction medium is stirred at AT for 16 hours. The reaction medium is poured into 50 ml of ice-cold water and the mixture is then extracted with DCM, washed with water, and then with a saturated NaCl solution. After drying over MgSO$_4$, the product obtained is chromatographed on silica, elution being carried out with an EtOAc/hexane mixture (10/90; v/v and then 20/80; v/v), and then with an MeOH/DCM mixture (3/97; v/v). The product obtained is crystallized from the isopropyl ether. 0.15 g of the expected product is obtained, Mp=165° C.

By carrying out the procedure according to Example 1 (steps 1.1 and 1.2), the intermediate compounds of formula (II) and (IIa) described below are prepared.

TABLE 1

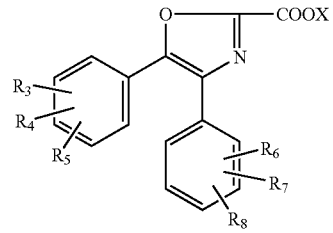

(II, IIa)

| Compound N° | R$_3$, R$_4$, R$_5$ | R$_6$, R$_7$, R$_8$ | X | Characterization (conditions) |
|---|---|---|---|---|
| 2.1 | 4-Br | 2,4-diCl | H | (a) MH$^+$ = 412 <br> rt = 10.94 |
| 3.1 | 2,4-diCl | 4-Cl | Et | (a) MH$^+$ = 396 <br> rt = 11.82 |
| 4.1 | 4-Cl | 2-Cl | Et | (a) MH$^+$ = 362 <br> rt = 11.00 |

EXAMPLE 2

Compound No. 17

1-(1-((4-(4-Chlorophenyl)-5-(2,4-dichlorophenyl)-1,3-oxazol-2-yl)carbonyl)-4-phenylpiperidin-4-yl)ethanone 1.58 ml of 2M trimethylaluminum in toluene are added, under cold conditions, to a solution of 0.64 g of 4-phenyl-4-acetylpiperidine in 2 ml of toluene, placed under nitrogen. The reaction medium is stirred for 1 hour at AT and then 0.5 g of the compound of preparation 1.1, dissolved in 2 ml of dry toluene, is added drop wise and the reaction medium is then heated at 60° C. for 2 hours. The reaction medium is allowed to return to AT and is then poured into water and the pH is adjusted to 5 by adding 5% HCl. The reaction medium is extracted twice with EtOAc, and then washing is carried out twice with a saturated NaCl solution. Drying is carried out over MgSO$_4$, followed by concentration to dryness. After purification, 460 mg of the expected compound are obtained, Mp=175.5-176.4.

The following table illustrates the chemical structures and the physical properties of some compounds of the invention. In this table, Ph, Me and Et represent, respectively, the phenyl, methyl and ethyl groups.

TABLE 2

(I)

| Compound N° | R₃, R₄, R₅ | R₆, R₇, R₈ | NR₁R₂ | Characterization (conditions) | Method of synthesis |
|---|---|---|---|---|---|
| 1 | 4-Cl | 2,4-diCl | —NH—N(piperidine) | Mp = 165° C. | A |
| 2 | 4-Cl | 2,4-diCl | N-methylpiperazine-N'-(3-chlorophenyl) | Mp = 174° C. (b) MH⁺ = 546 rt = 2.30 | A |
| 3 | 4-Cl | 2,4-diCl | 4-hydroxy-4-phenylpiperidin-1-yl | (b) MH⁺ = 527 rt = 2.41 | A |
| 4 | 4-Cl | 2,4-diCl | —NH—CH(CO₂Et)—CH₂—(4-Cl-C₆H₄) (+/−) | (b) MH⁺ = 577 rt = 2.56 | A |
| 5 | 4-Cl | 2,4-diCl | 4-(ethoxycarbonyl)piperidin-1-yl | (b) MH⁺ = 507 rt = 2.47 | A |
| 6 | 4-Cl | 2,4-diCl | —NH-(1-adamantyl) | (b) MH⁺ = 501 rt = 2.41 | A |
| 7 | 4-Cl | 2,4-diCl | —NH—N(octahydrocyclopenta[c]pyrrole) | (b) MH⁺ = 477 rt = 2.10 | A |
| 8 | 4-Cl | 2,4-diCl | —NH-(trimethylcyclohexyl) (+) | (b) MH⁺ = 503 rt = 2.36 | A |
| 9 | 4-Cl | 2,4-diCl | —NH—C(Me)₂—Et | (b) MH⁺ = 437 rt = 2.45 | A |
| 10 | 4-Cl | 2,4-diCl | —HN-(norbornyl) exo | (b) MH⁺ = 461 rt = 2.45 | A |

TABLE 2-continued

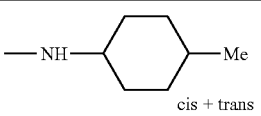

(I)

| Compound N° | R₃, R₄, R₅ | R₆, R₇, R₈ | NR₁R₂ | Characterization (conditions) | Method of synthesis |
|---|---|---|---|---|---|
| 11 | 4-Cl | 2,4-diCl | 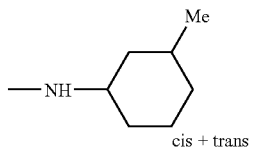 —NH—⟨cyclohexyl⟩—Me  cis + trans | (b) MH⁺ = 463  rt = 2.50 | A |
| 12 | 4-Cl | 2,4-diCl | 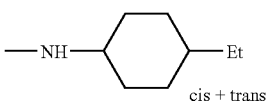 —NH—⟨cyclohexyl with Me⟩  cis + trans | (b) MH⁺ = 463  rt = 2.49 | A |
| 13 | 4-Cl | 2,4-diCl | 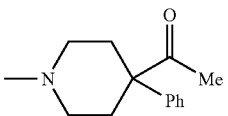 —NH—⟨cyclohexyl⟩—Et  cis + trans | (b) MH⁺ = 477  rt = 2.56 | A |
| 14 | 4-Br | 2,4-diCl | 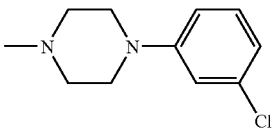 | Mp = 188-193° C.  (a) MH⁺ = 597  rt = 12.37 | A |
| 15 | 4-Br | 2,4-diCl | 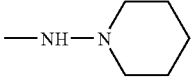 | Mp = 147-151° C.  (a) MH⁺ = 590  rt = 13.09 | A |
| 16 | 4-Br | 2,4-diCl | 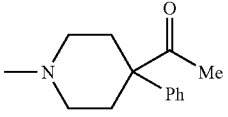 | Mp = 177-181° C.  (a) MH⁺ = 494  rt = 10.94 | A |
| 17 | 2,4-diCl | 4-Cl | 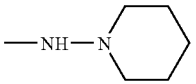 | Mp = 175° C.  (a) MH⁺ = 553  rt = 12.45 | B |
| 18 | 2,4-diCl | 4-Cl | 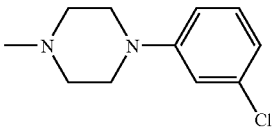 | Mp = 163° C.  (a) MH⁺ = 450  rt = 10.98 | B |
| 19 | 2,4-diCl | 4-Cl |  | Mp = 177-178° C.  (a) MH⁺ = 546  rt = 12.91 | B |
| 20 | 4-Cl | 2,4-diCl | —N⟨piperazine⟩N—Ph | Mp = 197° C.  (a) MH⁺ = 512  rt = 12.25 | B |

TABLE 2-continued (I)

| Compound N° | R₃, R₄, R₅ | R₆, R₇, R₈ | NR₁R₂ | Characterization (conditions) | Method of synthesis |
|---|---|---|---|---|---|
| 21 | 4-Cl | 2,4-diCl | piperazine-N-(3-methylphenyl) | Mp = 176° C.<br>(a) MH⁺ = 526<br>rt = 12.58 | B |
| 22 | 4-Cl | 2,4-diCl | 1-methyl-4-(4-chlorophenyl)-4-acetylpiperidine | Mp = 176° C.<br>(a) MH⁺ = 587<br>rt = 12.70 | B |
| 23 | 4-Cl | 2,4-diCl | 1-methyl-4-phenyl-4-(pyrrolidin-1-ylcarbonyl)piperidine | foam<br>(a) MH⁺ = 608<br>rt = 12.13 | B |
| 24 | 4-Cl | 2,4-diCl | 1-methyl-4-phenyl-4-carbamoylpiperidine | Mp = 194° C.<br>MH⁺ = 554<br>rt = 10.01 | A |
| 25 | 4-Cl | 2,4-diCl | piperazine-N-(3-methoxyphenyl) | Mp = 153° C.<br>MH⁺ = 542<br>rt = 12.21 | B |
| 26 | 4-Cl | 2,4-diCl | 1-methyl-4-phenyl-4-acetylpiperidine | Mp = 145° C.<br>MH⁺ = 553<br>rt = 11.52 | B |
| 27 | 4-Cl | 2,4-diCl | piperazine-N-(4-chlorophenyl) | Mp = 180° C.<br>(a) MH⁺ = 546<br>rt = 12.78 | B |
| 28 | 4-Cl | 2,4-diCl | piperazine-N-(4-acetylphenyl) | Mp = 239° C.<br>(a) MH⁺ = 554<br>rt = 11.56 | B |

TABLE 2-continued (I)

| Compound N° | R₃, R₄, R₅ | R₆, R₇, R₈ | NR₁R₂ | Characterization (conditions) | Method of synthesis |
|---|---|---|---|---|---|
| 29 | 4-Cl | 2,4-diCl | (piperidine-substituted N-methylpiperidine-4-carboxamide) | Mp = 230° C. (a) MH⁺ = 561 rt = 7.64 | A |
| 30 | 4-Cl | 2,4-diCl | (4-(3-fluorophenyl)-1-methylpiperazine) | Mp = 192° C. (a) MH⁺ = 530 rt = 12.41 | B |
| 31 | 4-Cl | 2,4-diCl | (4-(2-chlorophenyl)-1-methylpiperazine) | Mp = 143° C. (a) MH⁺ = 546 rt = 13.00 | B |
| 32 | 4-Cl | 2,4-diCl | (4-(3-cyanophenyl)-1-methylpiperidine) | Mp = 160° C. (a) MH⁺ = 536 rt = 12.08 | B |
| 33 | 4-Cl | 2,4-diCl | (1-methyl-4-phenylpiperidine-4-carbonitrile) | Mp = 194° C. (a) MH⁺ = 536 rt = 12.16 | B |
| 34 | 4-Cl | 2,4-diCl | (1'-methylspiro[indene-1,4'-piperidine]) | Mp = 215° C. (a) MH⁺ = 535 rt = 12.90 | A |
| 35 | 4-Cl | 2,4-diCl | (methyl 2-(1-methylpiperidin-4-yl)benzoate) | Mp = 96° C. (a) MH⁺ = 569 rt = 12.53 | A |
| 36 | 4-Cl | 2,4-diCl | (1'-methylspiro[isobenzofuran-1(3H),4'-piperidin]-3-one) | Mp = >250° C. (a) MH⁺ = 553 rt = 10.52 | A |

TABLE 2-continued (I)

[Structure of formula (I): oxazole core with CO—NR₁R₂ substituent, two phenyl rings bearing R₃, R₄, R₅ and R₆, R₇, R₈ substituents]

| Compound N° | R₃, R₄, R₅ | R₆, R₇, R₈ | NR₁R₂ | Characterization (conditions) | Method of synthesis |
|---|---|---|---|---|---|
| 37 | 4-Cl | 2,4-diCl | [piperidinyl substituted with 3-chlorophenyl] | Mp = 88° C. (a) MH⁺ = 545 rt = 13.14 | A |
| 38 | 4-Cl | 2-Cl | [piperidinyl with C(Me)(Ph)(C=O)] | F = 79° C. (a) MH⁺ 519 rt = 11.54 | B |
| 39 | 4-Cl | 2-Cl | [piperazinyl substituted with 3-chlorophenyl] | Mp = 59° C. (a) MH⁺ = 512 rt = 12.18 | B |

The compounds of formula (I) possess good affinity in vitro ($IC_{50}$ of between $10^{-6}$M and $10^{-9}$M) for cannabinoid $CB_1$ receptors, under the experimental conditions described by M. Rinaldi-Carmona et al. (FEBS Letters, 1994, 350, 240-244).

The antagonistic nature of the compounds of formula (I) was determined by means of the results obtained in the models of adenylate cyclase inhibition as described in M. Bouaboula et al., J. Biol. Chem., 1995, 270, 13973-13980; M. Rinaldi-Carmona et al., J. Pharmacol. Exp. Ther., 1996, 278, 871-878 and M. Bouaboula et al., J. Biol. Chem., 1997, 272, 22330-22339. All of the references described hereinabove are incorporated herein by reference in their entirety.

The toxicity of the compounds of formula (I) is compatible with their use as a medicinal product.

According to another of its aspects, the present invention relates to the use of a compound of formula (1), or of one of its pharmaceutically acceptable salts, solvates or hydrates, for preparing medicinal products intended to treat or prevent diseases involving cannabinoid $CB_1$ receptors.

For example and without implied limitation, the compounds of formula (I) are useful as psychotropic medicinal products, in particular for the treatment of psychiatric disorders including anxiety, depression, mood disorders, insomnia, deliria disorders, obsessive disorders, psychoses in general, schizophrenia, attention deficit hyperactivity disorder (ADHD) in hyperkinetic children, and also for the treatment of disorders associated with the use of psychotropic substances, in particular in the case of abuse of a substance and/or dependence on a substance, including alcohol dependency and nicotine dependency.

The compounds of formula (I) according to the invention may be used as medicinal products for the treatment of migraine, stress, diseases of psychosomatic origin, panic attacks, epilepsy, movement disorders, in particular dyskinesia or Parkinson's disease, trembling and dystonia.

The compounds of formula (I) according to the invention may also be used as medicinal products in the treatment of memory deficiencies, cognitive disorders, in particular in the treatment of senile dementia and Alzheimer's disease, and also in the treatment of attention or alertness disorders. Furthermore, the compounds of formula (I) may be useful as neuroprotective agents, in the treatment of ischemia, cranial traumas and the treatment of neurodegenerative diseases: including chorea, Huntington's chorea and Tourrette's syndrome.

The compounds of formula (I) according to the invention may be used as medicinal products in the treatment of pain: neuropathic pain, acute peripheral pain, and chronic pain of inflammatory origin.

The compounds of formula (I) according to the invention may be used as medicinal products in the treatment of appetite disorders, craving disorders (craving for sugars, carbohydrates, drugs, alcohol or any appetizing substance) and/or eating disorders, in particular as anorexigenic agents or for the treatment of obesity or bulimia, and also for the treatment of type II diabetes or non-insulin-dependent diabetes and for the treatment of dyslipidaemia and metabolic syndrome. Thus, the compounds of formula (I) according to the invention are useful in the treatment of obesity and the risks associated with obesity, in particular the cardiovascular risks. Furthermore, the compounds of formula (I) according to the invention may be used as medicinal products in the treatment of gastrointestinal disorders, diarrheic disorders, ulcers, vomiting, bladder and urinary disorders, disorders of endocrine origin, cardiovascular disorders, hypotension, hemorrhagic shock, septic shock, chronic liver cirrhosis, hepatic steatosis, steatohepatitis, asthma, chronic bronchitis, chronic obstructive bronchopneumopathy, Raynaud's syndrome, glaucoma, fertility disorders, inflammatory phenomena, immune system diseases, in particular autoimmune and neuroinflammatory diseases such as rheumatoid arthritis, reactional arthritis, diseases resulting in demyelinization, multiple sclerosis, infectious and viral diseases such as encephalitis, cerebral strokes, and also as medicinal products for anticancer chemotherapy, for treating Guillain-Barre syndrome and for treating osteoporosis.

According to the present invention, the compounds of formula (I) are most particularly useful for treating psychotic disorders, in particular schizophrenia; attention deficit hyperactivity disorders (ADHD) in hyperkinetic (MBD) children; for treating appetite disorders and obesity; for treating memory and cognitive deficiencies; for treating alcohol dependency and nicotine dependency, i.e. for alcohol withdrawal and for tobacco withdrawal.

According to one of its aspects, the present invention relates to the use of a compound of formula (I), of its pharmaceutically acceptable salts and of their solvates or hydrates, for treating the disorders and diseases indicated above.

The compound according to the invention is generally administered as a dosage unit.

Said dosage units are preferably formulated in pharmaceutical compositions in which the active principle is mixed with a pharmaceutical excipient.

Thus, according to another of its aspects, the present invention relates to pharmaceutical compositions containing, as active principle, a compound of formula (I), one of its pharmaceutically acceptable salts or one of their solvates or hydrates.

The compound of formula (I) above and its pharmaceutically acceptable salts or solvates may be used at daily doses of 0.01 to 100 mg per kg of body weight of the mammal to be treated, preferably at daily doses of 0.02 to 50 mg/kg. In humans, the dose may range preferably from 0.05 to 4000 mg per day, more particularly from 0.1 to 1000 mg per day, depending on the age of the individual to be treated or the type of treatment, i.e. prophylactic or curative. Although these dosages are examples of average situations, there may be specific cases where higher or lower dosages are appropriate; such dosages are also part of the invention. According to usual practice, the dosage appropriate for each patient is determined by the physician according to the mode of administration, and the age, the weight and the response of said patient.

In the pharmaceutical compositions of the present invention for oral, sublingual, inhaled, subcutaneous, intramuscular, intravenous, transdermal, local or rectal administration, the active principle can be administered in a unit form of administration, as a mixture with conventional pharmaceutical carriers, to animals and to human beings. The appropriate unit forms of administration include oral forms such as tablets, gelatin capsules, powders, granules and oral solutions or suspensions, sublingual and buccal administration forms, aerosols, topical administration forms, implants, subcutaneous, intramuscular, intravenous, intranasal or intraocular administration forms and rectal administration forms.

In the pharmaceutical compositions of the present invention, the active principle is generally formulated in dosage units containing from 0.05 to 1000 mg, advantageously from 0.1 to 500 mg, preferably from 1 to 200 mg of said active principle per dosage unit for daily administrations.

By way of example, a unit form of administration of a compound according to the invention in the form of a tablet may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:
1. A compound of the formula (I):

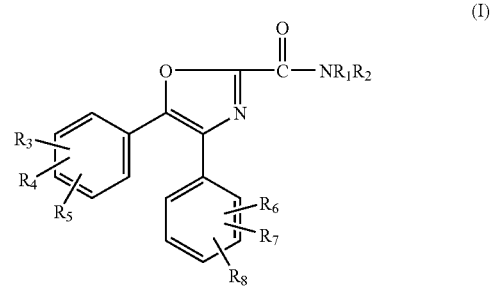

wherein:
R$_1$ represents hydrogen or (C$_1$-C$_4$)alkyl;
R$_2$ represents:
(C$_4$-C$_{10}$)alkyl;
a nonaromatic C$_3$-C$_{12}$ carbocyclic radical that is unsubstituted or substituted one or more times with (C$_1$-C$_4$) alkyl;
a 1,2,3,4-tetrahydronaphth-1yl or -2-yl;
a saturated, monooxygen or monosulfur-containing heterocyclic radical having from 5 to 7 atoms, that is unsubstituted or substituted one or more times with (C$_1$-C$_4$)alkyl;
a saturated, mononitrogen heterocyclic radical having from 5 to 7 atoms, the nitrogen atom being substituted with (C$_1$-C$_4$)alkyl, phenyl, benzyl, (C$_1$-C$_4$)alkoxycarbonyl or (C$_1$-C$_4$)alkanoyl group;
(C$_1$-C$_3$)alkylene group carrying a nonaromatic C$_3$-C$_{12}$ carbocyclic radial that is unsubstituted or substituted one or more times with (C$_1$-C$_4$) alkyl;
(C$_1$-C$_3$)alkylene, that is unsubstituted or substituted on the alkylene with one or more methyl or (C$_1$-C$_4$) alkoxycarbonyl groups, and unsubstituted or substituted on the phenyl with one or more substituents, that may be identical or different, chosen from halogen, (C$_1$-C$_4$)alkyl, trifluoromethyl, (C$_1$-C$_4$)alkoxy or trifluoromethoxy;
a group NR$_9$R$_{10}$;
or R$_1$ and R$_2$, together with the nitrogen atom to which they are attached, constitute:

either a piperazin-1-yl or 1,4-diazepan-1-yl radical substituted in the 4-position with a phenyl or benzyl group;

or a piperidin-1-yl or pyrrolidin-1-yl radical mono- or disubstituted with groups, that are identical or different, chosen from phenyl, benzyl, ($C_1$-$C_4$)alkyl, hydroxyl, cyano, ($C_1$-$C_3$)alkanoyl, ($C_1$-$C_4$)alkoxycarbonyl or ($C_1$-$C_4$)alkoxycarbonylamino group, or with a group $CONR_{11}R_{12}$ or $NR_{11}R_{12}$; and wherein said phenyl or benzyl is unsubstituted or substituted with one or more substituents chosen from halogen, methyl, hydroxyl, methoxy, cyano, acetyl or methoxycarbonyl;

or a spiro[1H-inden-1,4'-piperidine] radical or a 3H-spiro[2-benzofuran-1,4'-piperidine] radical, said radical being unsubstituted or substituted with an oxo group;

$R_3$, $R_4$, $R_5$, $R_6$, $R_7$ and $R_8$ each represent, independently of one another, a hydrogen or halogen atom, a ($C_1$-$C_6$)alkyl, ($C_1$-$C_6$)alkoxy or trifluoromethyl group or a group $S(O)_n$Alk; with the proviso that $R_3$, $R_4$, $R_5$, $R_6$, $R_7$ and $R_8$ are not simultaneously hydrogen;

$R_9$ represents hydrogen or methyl;

$R_{10}$ represents ($C_3$-$C_6$)alkyl, phenyl or ($C_3$-$C_{10}$)cycloalkyl, said phenyl and cycloalkyl being unsubstituted or substituted with one or more substituents chosen from halogen or ($C_1$-$C_4$)alkyl;

or $R_9$ and $R_{10}$, together with the nitrogen atom to which they are attached, constitute a saturated or unsaturated heterocyclic radical having from 5 to 11 atoms, which is optionally bridged, optionally comprising a spiro carbon and optionally containing a second hetero atom chosen from O or N, said radical being unsubstituted or substituted one or more times with a substituent group chosen from hydroxyl, ($C_1$-$C_4$)alkyl or ($C_1$-$C_4$)alkoxycarbonyl or phenyl that is unsubstituted or substituted with one or more substituents chosen from halogen or ($C_1$-$C_4$)alkyl;

$R_{11}$ and $R_{12}$ each represent, independently of one another, hydrogen or ($C_1$-$C_4$)alkyl;

or $R_{11}$ and $R_{12}$, together with the nitrogen atom to which they are attached, constitute a saturated heterocyclic radical having from 3 to 7 atoms, optionally containing a second hetero atom chosen from O or N, said heterocyclic radical being unsubstituted or substituted one or more times with methyl;

n represents 0, 1 or 2; and

Alk represents a ($C_1$-$C_4$)alkyl group; or a salt thereof, or a hydrate or a solvate of said compound or said salt.

2. The compound of formula (I) according to claim 1, wherein:

$R_1$ and $R_2$, together with the nitrogen atom to which they are attached, constitute:

either a piperazin-1-yl or 1,4-diazepan-1-yl radical substituted in the 4-position with a phenyl or benzyl group;

or a piperidin-1-yl or pyrrolidin-1-yl radical that is monosubstituted or gem-disubstituted with groups, that may be identical or different, chosen from phenyl, benzyl, ($C_1$-$C_4$)alkyl, hydroxyl, ($C_1$-$C_3$)alkanoyl, ($C_1$-$C_4$)alkoxycarbonyl or ($C_1$-$C_4$)alkoxycarbonylamino group; and wherein said phenyl or benzyl is unsubstituted or substituted with one or more substituents chosen from halogen or methyl;

$R_3$, $R_4$, $R_5$, $R_6$, $R_7$ and $R_8$ each represent, independently of one another, hydrogen, halogen, ($C_1$-$C_6$)alkyl, ($C_1$-$C_6$)alkoxy or trifluoromethyl group or a group $S(O)_n$Alk; with the proviso that $R_3$, $R_4$, $R_5$, $R_6$, $R_7$ and $R_8$ are not simultaneously hydrogen;

n represents 0, 1 or 2; and

Alk represents ($C_1$-$C_4$)alkyl; or a salt thereof, or a hydrate or a solvate of said compound or said salt.

3. The compound of formula (I) according to claim 1, wherein:

$R_1$ and $R_2$, together with the nitrogen atom to which they are attached, constitute:

either a piperazin-1-yl radical substituted in the 4-position with phenyl or benzyl;

or a piperidin-1-yl radical that is monosubstituted or disubstituted with phenyl, benzyl, ($C_1$-$C_4$)alkyl, hydroxyl, cyano, ($C_1$-$C_3$)alkanoyl, ($C_1$-$C_4$)alkoxycarbonyl or ($C_1$-$C_4$)alkoxycarbonylamino group, or with a group $CONR_{11}R_{12}$ or $NR_{11}R_{12}$; and wherein said phenyl or benzyl is unsubstituted or substituted with one or more substituents chosen from halogen, methyl, methoxy, cyano, acetyl or methoxycarbonyl;

or a spiro [1H-inden-1,4'-piperidine] radical or a 3H-spiro[2-benzofuran-1,4'-piperidine] radical, said radical being unsubstituted or substituted with an oxo group;

$R_{11}$ and $R_{12}$ each represent, independently of one another, hydrogen or ($C_1$-$C_4$)alkyl;

or $R_{11}$ and $R_{12}$, together with the nitrogen atom to which they are attached, constitute a saturated heterocyclic radical having from 3 to 7 atoms, optionally containing a second hetero atom chosen from O or N, said heterocyclic radical being unsubstituted or substituted one or more times with methyl; and $R_3$, $R_4$, $R_5$, $R_6$, $R_7$ and $R_8$ each represent, independently of one another, hydrogen or halogen; with the proviso that $R_3$, $R_4$, $R_5$, $R_6$, $R_7$ and $R_8$ are not simultaneously hydrogen atom; or a salt thereof, or a hydrate or a solvate of said compound or said salt.

4. The compound of formula (I) according to claim 1, wherein:

$R_1$ and $R_2$, together with the nitrogen atom to which they are attached, constitute:

either a piperazin-1-yl radical substituted in the 4-position with phenyl;

or a piperidin-1-yl radical that is unsubstituted or gem-disubstituted with phenyl or piperidin-1-yl, and with cyano, acetyl, aminocarbonyl or pyrrolidin-1-ylcarbonyl group; and wherein said phenyl is unsubstituted or substituted with chlorine, bromine, fluorine, methyl, methoxy, hydroxyl, cyano or acetyl;

or a spiro[1H-inden-1,4'-piperidine] radical;

or a 3H-spiro[2-benzofuran-1,4'-piperidin]-3-one radical;

$R_3$ is 4-bromo or 4-chloro;

$R_6$ is 2-chloro;

$R_7$ is 4-chloro or hydrogen; and $R_4$, $R_5$ and $R_8$ represent hydrogen; or a salt thereof, or a hydrate or a solvate of said compound or said salt.

5. The compound of formula (I) according to claim 1, which is chosen from:

1-{[5-(4-Chlorophenyl)-4-(2,4-dichlorophenyl)-1,3-oxazol-2-yl]carbonyl}-4-(3-methylphenyl)piperazine;

1-{[5-(4-Chlorophenyl)-4-(2,4-dichlorophenyl)-1,3-oxazol-2-yl]carbonyl}-4-(3-methoxyphenyl)piperazine;

1-{[5-(4-Chlorophenyl)-4-(2,4-dichlorophenyl)-1,3-oxazol-2-yl]carbonyl}-4-chlorophenyl)piperazine;

1-{[5-(4-Chlorophenyl)-4-(2,4-dichlorophenyl)-1,3-oxazol-2-yl]carbonyl}-4-(3-fluorophenyl)piperazine;

1-{[5-(4-Chlorophenyl)-4-(2,4-dichlorophenyl)-1,3-oxazol-2-yl]carbonyl}-4-(2-chlorophenyl)piperazine;

1-(4-(4-Chlorophenyl)-1-{[5-(4-chlorophenyl)-4-(2,4-dichlorophenyl)-1,3-oxazol-2-yl]carbonyl}piperidin-4-yl)ethanone;

1-{[5-(4-Chlorophenyl)-4-(2,4-dichlorophenyl)-1,3-oxazol-2-yl]carbonyl}-4-phenylpiperidine-4-carboxamide;

1-[4-(4-{[5-(4-Chlorophenyl)-4-(2,4-dichlorophenyl)-1,3-oxazol-2-yl]carbonyl}piperazin-1-yl)phenyl]ethanone;

1'-{[5-(4-Chlorophenyl)-4-(2,4-dichlorophenyl)-1,3-oxazol-2-yl]carbony}-1,4'-bipiperidine-4'-carboxamide;

1-(1-{[4-(2-Chlorophenyl)-5-(4-chlorophenyl)-1,3-oxazol-2-yl]carbonyl}-4-phenylpiperidin-4-yl)ethanone;

1-{[5-(4-Chlorophenyl)-4-(2,4-dichlorophenyl)-1,3-oxazol-2-yl]carbonyl}-4-phenylpiperidine-4-carbonitrile;

1-(3-Chlorophenyl)-4-{[4-(2-chlorophenyl)-5-(4-chlorophenyl)-1,3-oxazol-2-yl]carbonyl}piperazine;

1'-{[5(4-Chlorophenyl)-4-(2-chlorophenyl)-1,3-oxazol-2-yl]carbonyl}-1,4'-bipiperidine-4'-carboxamide;

1-(1-{[5-(4-Bromophenyl)-4-(2,4-dichlorophenyl)-1,3-oxazol-2-yl]carbonyl}-4-phenylpiperidin-4-yl)ethanone;

1-(1-{[5-(4-Bromophenyl)-4-(2,4-dichlorophenyl)-1,3-oxazol-2-yl]carbonyl}-4-(3-chlorophenyl)piperazine; and 1-(1-{[5-(4-Chlorophenyl)-4-(2,4-dichlorophenyl)-1,3-oxazol-2-yl]carbonyl}-4-phenylpiperidin-4-yl)ethanone; or a salt thereof, or a hydrate or a solvate of said compound or said salt.

6. A process for preparing a compound of formula (I) according to claim 1, comprising the step of:

reacting an acid of formula (II) or a functional derivative of said acid:

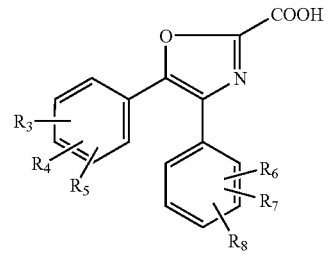

with an amine of formula $HNR_1R_2$ (III) wherein $R_1$, $R_2$, $R_3$, $R_4$, $R_5$, $R_6$, $R_7$ and $R_8$ are as defined in claim 1.

7. A pharmaceutical composition comprising a compound of formula (I) according to claim 1, or a pharmaceutically acceptable salt thereof, or a pharmaceutically acceptable hydrate or a solvate of said compound or said salt, in combination with at least one pharmaceutically acceptable excipient.

8. A pharmaceutical composition comprising a compound of formula (I) according to claim 2, or a pharmaceutically acceptable salt thereof, or a pharmaceutically acceptable hydrate or a solvate of said compound or said salt, in combination with at least one pharmaceutically acceptable excipient.

9. A pharmaceutical composition comprising a compound of formula (I) according to claim 3, or a pharmaceutically acceptable salt thereof, or a pharmaceutically acceptable hydrate or a solvate of said compound or said salt, in combination with at least one pharmaceutically acceptable excipient.

10. A pharmaceutical composition comprising a compound of formula (I) according to claim 4, or a pharmaceutically acceptable salt thereof, or a pharmaceutically acceptable hydrate or a solvate of said compound or said salt, in combination with at least one pharmaceutically acceptable excipient.

11. A pharmaceutical composition comprising a compound of formula (I) according to claim 5, or a pharmaceutically acceptable salt thereof, or a pharmaceutically acceptable hydrate or a solvate of said compound or said salt, in combination with at least one pharmaceutically acceptable excipient.

* * * * *